(12) United States Patent
Wolf et al.

(10) Patent No.: US 9,301,780 B2
(45) Date of Patent: Apr. 5, 2016

(54) CATHETER, IN PARTICULAR FOR IMPLANTING AN EMBRYO IN THE UTERINE CAVITY OF A HUMAN BEING OR ANIMAL, AND CORRESPONDING INSTRUMENT

(75) Inventors: Jean-Philippe Wolf, Paris (FR); Christophe Poncelet, Taverny (FR)

(73) Assignees: Assistance Publique—Hopitaux De Paris, Paris (FR); Universite Paris Descartes, Paris (FR); Universite Paris 13, Villetaneuse (FR)

( * ) Notice: Subject to any disclaimer, the term of this patent is extended or adjusted under 35 U.S.C. 154(b) by 513 days.

(21) Appl. No.: 13/255,065

(22) PCT Filed: Mar. 1, 2010

(86) PCT No.: PCT/FR2010/050346
§ 371 (c)(1),
(2), (4) Date: Mar. 5, 2012

(87) PCT Pub. No.: WO2010/100373
PCT Pub. Date: Sep. 10, 2010

(65) Prior Publication Data
US 2012/0172660 A1    Jul. 5, 2012

(30) Foreign Application Priority Data

Mar. 4, 2009 (FR) ..................................... 09 51354

(51) Int. Cl.
*A61B 17/435* (2006.01)
*A61M 25/00* (2006.01)

(52) U.S. Cl.
CPC ............ *A61B 17/435* (2013.01); *A61M 25/007* (2013.01); *A61M 25/0023* (2013.01); *A61M 2025/0081* (2013.01)

(58) Field of Classification Search
CPC ...... A61B 17/42; A61B 17/425; A61B 17/43; A61B 17/435; A61D 19/04; A61M 25/007; A61M 31/00; A61M 31/005; A61M 2025/0042
USPC ........................ 600/33–35; 604/514–517, 906
See application file for complete search history.

(56) References Cited

U.S. PATENT DOCUMENTS

| | | | |
|---|---|---|---|
| 4,642,094 A | | 2/1987 | North et al. |
| 6,610,005 B1 * | | 8/2003 | Tao .................................. 600/34 |
| 6,838,050 B1 * | | 1/2005 | Green et al. .................... 422/37 |
| 2003/0050531 A1 | | 3/2003 | Field |
| 2005/0215849 A1 * | | 9/2005 | Choay et al. .................... 600/33 |
| 2006/0264809 A1 * | | 11/2006 | Hansmann et al. ............. 604/22 |

(Continued)

FOREIGN PATENT DOCUMENTS

| | | |
|---|---|---|
| EP | 478155 | 4/1992 |
| FR | 2715824 | 8/1995 |

(Continued)

*Primary Examiner* — Charles A Marmor, II
*Assistant Examiner* — Carrie R Dorna
(74) *Attorney, Agent, or Firm* — Thompson Coburn LLP

(57) ABSTRACT

This catheter comprises a tubular catheter body defining a longitudinal channel, the distal end of the catheter body being closed, and the channel opening out through a single side orifice onto an external surface of a side wall of the catheter body at a distance from this distal end. The channel includes a curved distal end segment and has a substantially constant diameter along the entire length thereof.

8 Claims, 3 Drawing Sheets

(56) References Cited

U.S. PATENT DOCUMENTS

Figure 1:
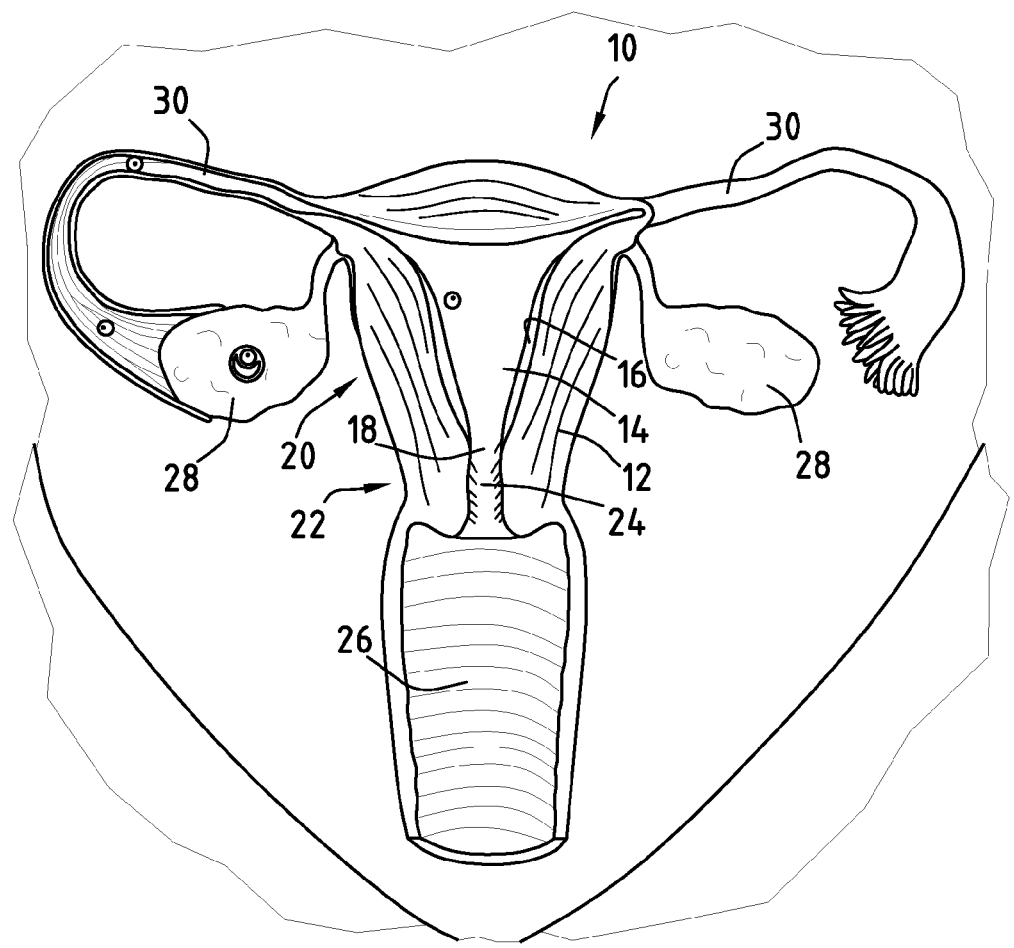

2007/0073275 A1* 3/2007 Conston et al. .................. 606/6
2008/0200752 A1* 8/2008 Inaudi .............................. 600/34

FOREIGN PATENT DOCUMENTS

GB 2 118 840 11/1983
WO 99/37348 7/1999

* cited by examiner

_CATHETER, IN PARTICULAR FOR IMPLANTING AN EMBRYO IN THE UTERINE CAVITY OF A HUMAN BEING OR ANIMAL, AND CORRESPONDING INSTRUMENT_

FIELD OF THE INVENTION

The present invention relates to a catheter, notably for implanting embryos in a uterine cavity of a human being or animal, of the type comprising a tubular catheter body defining a longitudinal channel.

BACKGROUND OF THE INVENTION

Embryo transfer remains a blind and non-physiological procedure. Indeed it is practiced through a transcervical route with a catheter of the aforementioned type, which is introduced through the endocervical canal in order to penetrate into the uterine cavity, which is lined with an endometrium at the maximum of its development. It is therefore not impossible that this operation may traumatize the endometrial mucosa and compromise the chances of successful transfer.

Endometrial lesions caused by present catheters may therefore interfere with the implantation of an embryo if the latter is deposited at the surface of the blood layer, which is the case with a conventional catheter.

SUMMARY OF THE INVENTION

The object of the invention is to propose a catheter with which the conditions of the embryo/endometrium interface may be improved in order to promote embryo implantation.

For this purpose, the object of the invention is a catheter of the aforementioned type, characterized in that:
  the distal end of the catheter body is closed,
  the channel opens out through a single side orifice on an external surface of a side wall of the catheter body, at a distance from this distal end,
  the channel includes a curved distal end segment, and
  the channel has a substantially constant diameter over the whole of its length.

The catheter according to the invention may include one or more of the following features:
  the diameter of the channel is substantially greater than 150 µm and less than 200 µm;
  the catheter comprises, in the vicinity of the proximal end of the catheter body, a mark of the angular position of the orifice;
  the distal end of the catheter body has a rounded shape without any sharp edges;
  the catheter comprises an endpiece attached on the proximal end of the catheter body and suitable for receiving injection means;
  the catheter comprises a metal insert positioned in the vicinity of the distal end of the catheter body;
  the catheter body is made from flexible plastic material suitable so as to be able to be bent manually;
  the curved distal end segment is substantially a circular arc; and
  the catheter body is made from a hydrophobic material.

The object of the invention is also an instrument notably for implanting embryos in a uterine cavity of a human being or animal, of the type comprising a catheter and injection means which may be connected to the proximal end of the catheter, characterized in that the catheter is as described earlier.

BRIEF DESCRIBTION OF THE DRAWINGS

Figure 2:
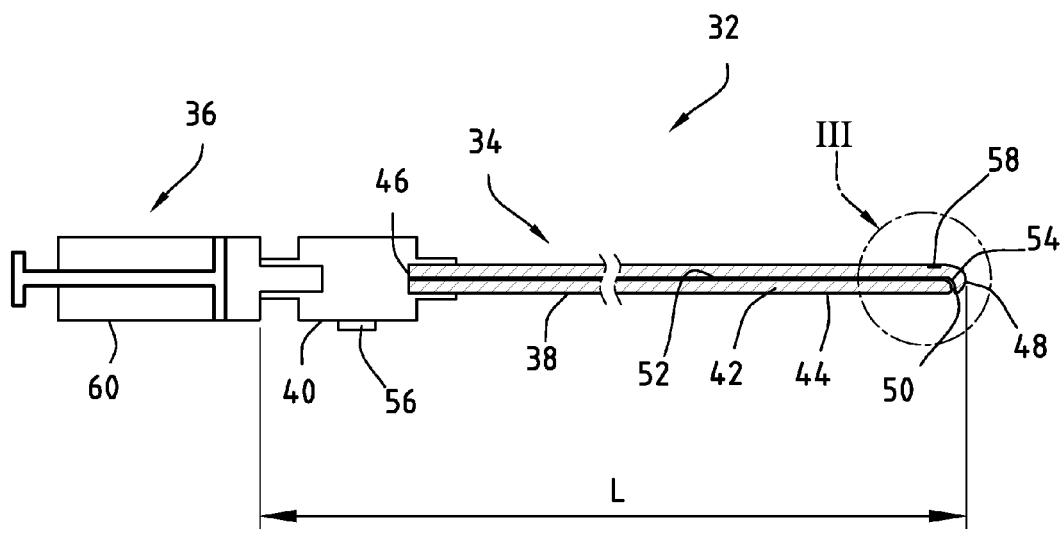
Figure 3:
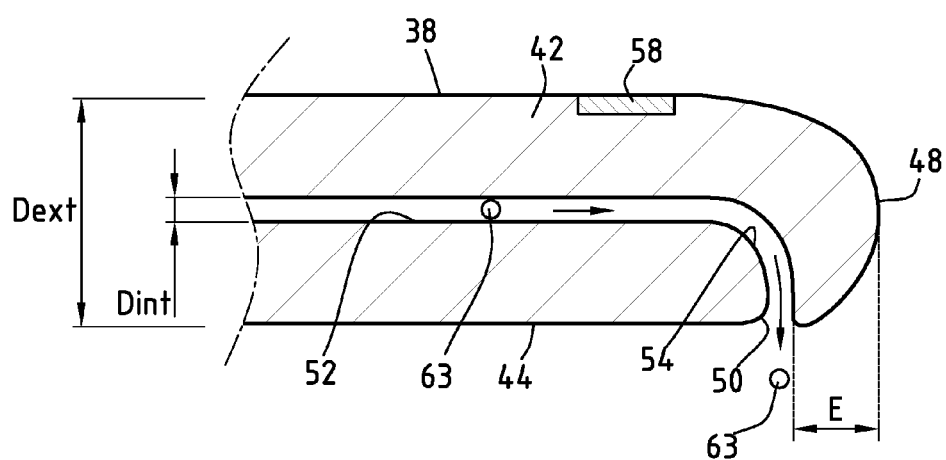
Figure 4:
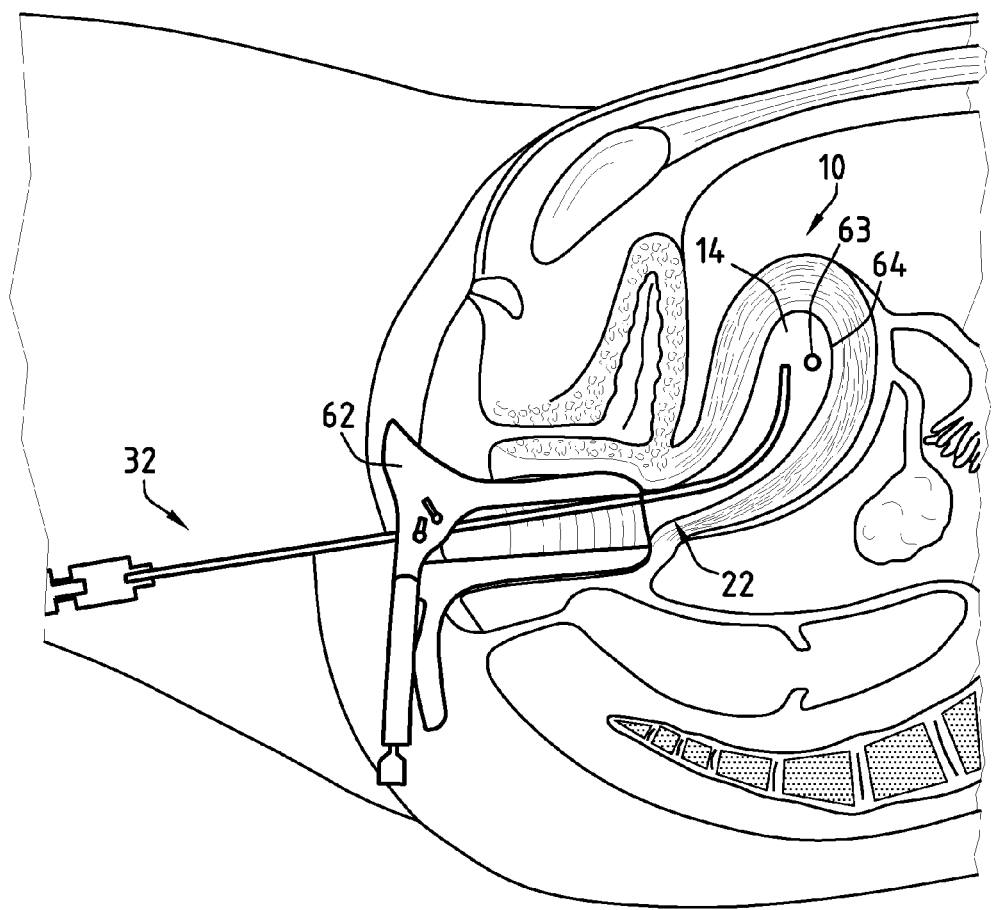

The invention will be better understood upon reading the following description, only given as an example and made with reference to the appended drawings, wherein:
  FIG. 1 is a front sectional view of a uterus;
  FIG. 2 is a longitudinal sectional view of an embryo transfer instrument provided with a catheter according to the invention;
  FIG. 3 is an enlarged view of the detail indicated as III in FIG. 2; and
  FIG. 4 is a side sectional view of the uterus of FIG. 1 into which the instrument of FIG. 2 is introduced.

DETAILED DESCRIBTION OF THE INVENTION

In order to better understand the description which follows, a few reminders of female anatomy are given with reference to FIG. 1, in which a uterus 10 is illustrated.

The uterus 10 is a hollow muscular organ intended to contain a fertilized egg during its development and to expel it when it has reached maturity. In other words, it is an organ in which an embryo develops, followed by the corresponding fetus, and which expels the latter upon delivery.

The muscle forming the uterus 10 is called the myometrium 12, the cavity which is found inside this muscle is called the uterine cavity 14 and the mucosa which lines the uterine cavity 14 is called the endometrium 16.

The uterus 10 has the shape of a cone with a truncated top directed downwards. Between the base and the top of the uterus 10, a slight constriction called the uterine isthmus 18 separates the uterus into two portions: an upper portion called the uterine body 20 and a lower portion called the cervix 22.

The cervix 22 is pierced in its middle with a canal called the endocervical canal 24 which connects the uterine cavity 14 to the vaginal cavity 26.

The uterus 10 is connected on each side to an ovary 28 through a Fallopian tube 30.

An embryo transfer consists of depositing delicately one or more embryos fertilized in the laboratory, for example by a conventional in vitro fertilization technique (IVF) or by an ICSI (Intra Cytoplasmic Sperm Injection) technique, into the uterine cavity 14 by means of a catheter.

If the development of the embryos continues normally, they will be implanted in the endometrium 16 provided that the latter is adequate.

FIG. 2 schematically illustrates an embryo transfer instrument 32 according to the invention.

The instrument 32 comprises a catheter 34 and injection means 36 which may be connected to the catheter 34.

The catheter 34 comprises a catheter body 38 and an endpiece 40 attached to the proximal end of the body 38.

The catheter body 38 has a cylindrical tubular shape defined by a cylindrical side wall 42 having an external surface 44, and has a proximal end 46 and a distal end 48.

As this is better seen in FIG. 3, a single side orifice 50 is made in the side wall 42 at a distance E from the distal end 48 substantially equal to 2 mm.

The catheter body 38 delimits a longitudinal internal channel 52 which extends from the proximal end 46 as far as the vicinity of the distal end 48.

The channel 52 is substantially rectilinear and includes a curved distal end segment 54, substantially as a quadrant.

The segment 54 opens out towards the outside of the catheter body 38 through the orifice 50, and substantially perpendicularly to the axis of the catheter 34 which corresponds to the axis of the channel 52.

The channel 52 has a substantially constant diameter Dint over the whole of its length and is comprised between 150μm (a value substantially corresponding to the size of an embryo) and 200 μm.

Thus, if several embryos are taken up, they will necessarily be positioned in the channel 52, following each other.

Alternatively, in the case when the instrument is used for blastocyst transfer, a channel 52 is provided having a substantially constant diameter Dint over the whole of its length and comprised between 200 μm (a value substantially corresponding to the size of a blastocyst) and 250 μm.

The distal end 48 of the catheter body 38 is closed and has a smooth rounded shape without any sharp edge and bump, substantially a half sphere.

The catheter body 38 has an external diameter Dext equal to 1.5 mm and is made from a flexible plastic material so as to be able to be bent manually by a practitioner so as to adapt to the anatomy of the patient.

Of course, the plastic material used is also biocompatible with the human body.

Preferably, the material used for making the catheter body 38 is hydrophobic, in order to limit the risks of the embryo adhering in the channel 52.

The endpiece 40 is sealably attached onto the proximal end 46 of the catheter body 38 and receives the injection means 36.

A mark 56 of the angular position of the orifice 50 (FIG. 2), for example a fin, is indicated on the endpiece 40.

The catheter 34 comprises an echo-guiding metal insert 58 positioned inside the side wall 42 of the catheter body 38, in proximity to the distal end 48.

The catheter 34, including the catheter body 38 and the endpiece 40 has a length L of the order of about 20 centimeters, preferably less than 22 cm.

The injection means 36 comprise a syringe 60 sealably connected to the endpiece 40 and having a capacity of 1 mL.

An embryo transfer procedure using the instrument 32 will now be described with reference to FIG. 4.

The patient is installed in the lithotomy position.

The practitioner puts in a speculum 62 so as to view the cervix 22 and cleans the latter.

By means of an echographic probe placed on the stomach, the practitioner locates the uterus 10.

Depending on the anatomy of the patient, the practitioner may slightly bend or not the distal end portion of the catheter 34 so as to facilitate the introduction of the instrument 32 into the uterus 10.

The practitioner then has the instrument 32, containing the embryo(s) 63 in a few microliters of culture medium, pass through the cervix 22 so that the distal end 48 is positioned in the uterine cavity 14.

The number of embryos to be transferred is generally one, in order to avoid multiple pregnancies.

The advance of the instrument 32 into the uterus 10 is performed with echographic inspection by means of the probe and is locatable by means of the metal insert 58.

Once the distal end 48 almost reaches the bottom of the uterine cavity 14, the practitioner orients the orifice 50 with the mark 56 in the direction of the postero-fundal wall 64 of the uterine cavity 14, which seems to be the ideal location for development of embryos.

Alternatively, the practitioner may decide to deposit the embryo(s) in any other location which seems to be more indicated to him/her.

It is then sufficient that the practitioner actuate the syringe 60 in order to expel the embryos.

Finally the practitioner slowly removes the instrument 32 from the uterus 10.

The invention therefore proposes an embryo transfer instrument with which it is possible to improve the success of medical assistance for reproduction by depositing the embryos at a distance from the path of the catheter and not in its axis.

The side positioning of the single orifice at a distance from the distal end not only gives the possibility of moving the embryos away from possible endometrial lesions generated by the introduction of the catheter into the uterus, but also selectively expelling the embryos towards an ideal implantation area.

Further, the rounded and smooth shape of the distal end of the catheter gives the possibility of making the introduction of the instrument less traumatizing for the endometrium.

The embryos used may be embryos originating from in vitro fertilization, from fertilization by ICSI or further frozen embryos.

The instrument according to the invention may also have a veterinary use by applying the embryo transfer into the uterine cavity of a female animal.

The invention claimed is:

1. An embryo transfer method for implanting embryos in a uterine cavity of a human being or animal using a catheter comprising a tubular catheter body defining a longitudinal channel, wherein:
   the tubular catheter body has a proximal end and a distal end, the distal end of the tubular catheter body being closed;
   the channel opens out through a single side orifice on an external surface of a side wall of the catheter body, at a distance from said distal end;
   the channel includes a curved distal end segment;
   the channel has a length, and it has a substantially constant diameter over its whole length; and
   the diameter of the channel is substantially greater than 150 μm and less than 200 μm;
wherein the method comprises positioning several embryos in the channel, following each other, then depositing embryos into the uterine cavity by means of the catheter, one after the other.

2. The method of claim 1, wherein the catheter further comprises, in a vicinity of the proximal end of the tubular catheter body, a mark of an angular position of the orifice.

3. The method of claim 1, wherein the distal end of the tubular catheter body has a rounded shape without any sharp edge.

4. The method of claim 1, wherein the catheter further comprises an endpiece attached on the proximal end of the tubular catheter body and adapted for receiving an injection element.

5. The method of claim 1, wherein the catheter further comprises a metal insert positioned in a vicinity of the distal end of the tubular catheter body.

6. The method of claim 1, wherein the tubular catheter body is made from a flexible plastic material adapted so as to be able to be bent manually.

7. The method of claim 1, wherein the curved distal end segment is a circular arc.

8. The method of claim 1, wherein the tubular catheter body is made from a hydrophobic material.

* * * * *